United States Patent [19]
Prybyla

[11] Patent Number: 6,045,582
[45] Date of Patent: Apr. 4, 2000

[54] IMPLANTABLE HUMERAL SHOULDER PROSTHESIS HAVING EXTENDED ARTICULAR SURFACE

[75] Inventor: Robert G. Prybyla, Round Rock, Tex.

[73] Assignee: Sulzer Orthopedics Inc., Austin, Tex.

[21] Appl. No.: 09/163,065

[22] Filed: Sep. 25, 1998

[51] Int. Cl.⁷ ..................................................... A61F 2/40
[52] U.S. Cl. ............................................. 623/19; 623/18
[58] Field of Search ................................. 623/18, 19, 21, 623/23

[56] References Cited

U.S. PATENT DOCUMENTS

| | | |
|---|---|---|
| 4,865,605 | 9/1989 | Dines et al. ............................... 623/19 |
| 4,865,609 | 9/1989 | Roche ...................................... 623/23 |
| 4,919,670 | 4/1990 | Dale et al. ................................ 623/19 |
| 4,964,865 | 10/1990 | Burkhead et al. ......................... 623/19 |
| 5,080,673 | 1/1992 | Burkhead .................................. 623/19 |
| 5,080,685 | 1/1992 | Bolesky et al. ........................... 623/23 |
| 5,314,479 | 5/1994 | Rockwood, Jr. et al. ................. 623/19 |
| 5,358,526 | 10/1994 | Tornier ..................................... 623/19 |
| 5,489,309 | 2/1996 | Lackey et al. ............................. 623/19 |
| 5,741,335 | 4/1998 | Gerber et al. ............................. 623/19 |
| 5,910,171 | 6/1999 | Kummer et al. .......................... 623/19 |

FOREIGN PATENT DOCUMENTS 617934  10/1994  European Pat. Off. ................. 623/19

Primary Examiner—Bruce E. Snow
Attorney, Agent, or Firm—Philip S. Lyren; Kenneth S. Barrow

[57] ABSTRACT

An implantable humeral shoulder prosthesis includes a stem and a head. The stem includes a distal stem portion having a longitudinal axis and a proximal body, and a first connector having an axis disposed at an acute angle relative to the longitudinal axis. The head includes an undersurface and a spherical articulating surface having a center. The undersurface includes a second connector having an axis that does not pass through the center. The articulating surface subtends a greater angle in a first plane including the axis of the second connector than in a second plane including the axis of the second connector. The first and second connectors are mutually engageable to interlock the head to the proximal body.

17 Claims, 1 Drawing Sheet

IMPLANTABLE HUMERAL SHOULDER PROSTHESIS HAVING EXTENDED ARTICULAR SURFACE

BACKGROUND OF THE INVENTION

1. Field of the Invention

The present invention relates generally to implantable orthopedic prostheses for replacing human skeletal joints, and relates more particularly to humeral components of implantable orthopedic shoulder prostheses for reconstructing a shoulder joint in a human.

2. Background of the Related Art

Implantable orthopedic prostheses, in one form, comprise man-made replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip, knee and shoulder joints are most often treated with such prostheses. The performance of each of these joints has an important effect on quality of life. The hip and knee joints play a critical role in ambulation and the shoulder joint plays a critical role in manual dexterity, resulting in great demand for surgical correction of abnormalities of these joints.

As used herein, the words proximal and distal are terms of reference that indicate a particular portion of a bone or prosthesis component according to the relative disposition of the natural bone or implanted prosthesis. Proximal indicates that portion of a component nearest the torso, whereas distal indicates that portion of a component farthest from the torso. Directional terms of reference used herein include superior, inferior, anterior, posterior, medial and lateral, which are used according to their commonly understood anatomical meanings. More particularly, with regard to a person in a standing position, superior means upward, inferior means downward, anterior means forward, posterior means rearward, medial means inwardly from the side toward the center of the body, and lateral means outwardly from the center of the body toward the side.

The human shoulder joint involves two bones: the humerus and the scapula, each having a smooth articulation surface arranged for articulation against an adjacent articulation surface of the other bone. The humerus includes at its proximal extremity a head having a convex, nearly hemi-spherically contoured articulation surface. With the arm in its natural position hanging adjacent the torso, the axis of the hemi-spherically contoured head is directed generally superiorly, medially, and posteriorly. The axis of the head forms an angle of about 45° to the superior-inferior axis, and an angle of about 35° to the medial-lateral axis. These angles are typical and can vary considerably between individuals. The articulating hemispherical surface of the head is covered with smooth cartilage. The scapula, in pertinent part, includes a bony formation known as the scapula head located on the superior lateral border. A glenoid cavity is located between the acromion process and the coracoid process of the scapula head. The glenoid cavity is a shallow, pear shaped, concave surface opening laterally and anteriorly, and elongated in the superior-inferior direction. The glenoid cavity is covered with smooth cartilage against which the head of the humerus articulates.

Shoulder prostheses typically include a stem to be implanted within the proximal medullary canal of a humerus, the medullary canal having been exposed by surgical resection of the natural humeral head. The stem includes a head affixed to the proximal end of the stem and having a spherical surface to engage and articulate against the glenoid cavity of the scapula. Prior humeral prostheses have been assembled from modular components comprising separate stem and head members. Connection between the head and stem usually is accomplished with mating male and female conical tapers, also known as Morse tapers. The mating conical tapers provide a firm and durable connection, yet permit the stem and head components to be disassembled from each other, if desired. Sometimes, a prosthetic glenoid component is also implanted against the scapula to provide a prosthetic articulating surface against which the head can articulate. Typically, stems are provided in a range of sizes involving variations in length and diameter, and heads are provided in a range of sizes involving variations in diameter and radius of curvature of the spherical articulating surface. Each of the various stems and heads employs commonly dimensioned conical taper surfaces to ensure interchangeability and modularity. The male conical taper can be disposed on the humeral stem, with the female conical taper disposed on the undersurface of the head, or vice versa.

Typical prior modular humeral shoulder stem prostheses have included a stem having a distal stem portion and a proximal body. The distal stem portion is generally cylindrical and elongate, whereas the proximal body is generally trapezoidal to approximate the shape of the proximal medullary canal of the humerus. The proximal body can have a planar portion disposed generally transversely to the axis of the natural humeral head, at an angle of about 45° to the longitudinal axis of the distal stem portion. A male conical taper can extend perpendicularly from the planar portion. Conversely, a female conical taper can be depressed in the planar portion.

Typical prior modular humeral shoulder head prostheses have included a generally planar undersurface. A female conical taper can lie depressed in the planar undersurface of the head for receiving the male conical taper of the humeral stem. When so received, the planar undersurface of the head lies adjacent the planar portion of the proximal body of the humeral stem. Conversely, the head prosthesis can include a male conical taper extending perpendicularly from the generally planar undersurface for mating with a humeral stem in which the proximal body includes a female conical taper. The articulating surface of the head, disposed opposite the planar undersurface, typically comprises a portion of a sphere subtending an angle less than 180° and intersecting the planar undersurface circumferentially. Usually, the conical taper connectors are coaxial with the axis of symmetry of the spherical articulating surface, and centered with respect to the planar undersurface of the head.

Prior humeral shoulder prosthesis configured as described above are generally satisfactory for most human patients. In some patients, however, certain disadvantages of the above-described configuration have been noted. Firstly, the superior edge of the head prosthesis may extend beyond the proximal humerus, creating undue stress on the rotator cuff muscles. Secondly, the inferior edge of the head prosthesis may contact the glenoid, or glenoid prosthesis, during some portions of the range of motion of the shoulder joint. Such contact happens especially when the arm is close to the torso, creating an "edge contact" between the head prosthesis and glenoid which accelerates wear of the articulating components. Thirdly, some patients have an anatomical condition in which the posterior cortical bone at the superior end of the humerus extends excessively posteriorly of the center of the medullary canal. In such patients, since the location of the head is dictated by the location of the stem in the medullary canal, the head of the humeral prosthesis may be located too far anteriorly to cover the posterior cortical bone.

It would be desirable to provide a modular, humeral shoulder prosthesis that can alleviate each of the mentioned disadvantages of prior prostheses, thereby permitting a wider range of anatomical variations to be accommodated. The present invention, particular embodiments of which are shown and described below, provides these and other desirable advantages.

SUMMARY OF THE INVENTION

According to one aspect of the invention, an implantable humeral shoulder prosthesis includes a stem and a head. The stem includes a distal stem portion having a longitudinal axis and a proximal body, and a first connector having an axis disposed at an acute angle relative to the longitudinal axis. The head includes an undersurface and a spherical articulating surface having a center. The undersurface includes a second connector having an axis that does not pass through the center. The articulating surface subtends a greater angle in a first plane including the axis of the second connector than in a second plane including the axis of the second connector. The first and second connectors are mutually engageable to interlock the head to the proximal body.

It is an object of the invention to accommodate a wider range of anatomical variations than have been accommodated by prior prostheses.

Other objects and advantages of the present invention will be apparent to one skilled in the pertinent art from the following descriptions of a preferred embodiment made with reference to the drawings.

DETAILED DESCRIPTION OF THE PREFERRED EMBODIMENT

Figure 2:
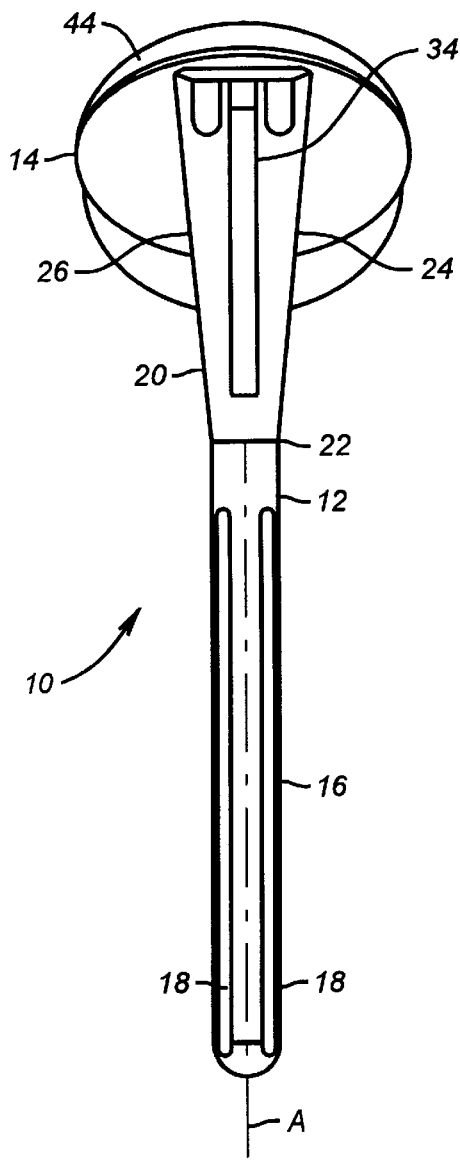
FIG. 2 is a rear elevation view of the humeral prosthetic stem and head of FIG. 1.

Referring to FIGS. 1, 2, 3 and 4, there is shown a modular humeral prosthesis 10 comprising a stem 12 and a head 14. The stem 12 is a unitary structure composed of a metal such as cobalt chromium alloy, or titanium alloy, or other biocompatible metal or material. The stem 12 includes a distal portion 16 that is substantially cylindrical and elongated, and sized to be inserted within the medullary canal at the proximal end of a human humerus. Stem 12 also includes a proximal body 20 providing a transition from the round cross-section of distal portion 16 to a substantially trapezoidal cross-section, shown in FIG. 4, sized and shaped to conform generally to the natural bone anatomy of the proximal medullary canal of a human humerus.

The distal portion 16 has a length within the range of about three inches to about six inches, and a diameter within the range of about 0.25 inches to about 0.75 inches. Stem 12 can be secured within the medullary canal with bone cement.

As preferred, distal portion 16 is longitudinally fluted to provide an escape path for the flow of bone cement as stem 12 is inserted into a prepared medullary canal into which bone cement has been introduced. The fluted configuration is provided by a plurality of longitudinal, shallow, round-bottomed grooves 18 depressed below the cylindrical surface of distal portion 16. Grooves 18 also provide enhanced adhesion between the bone cement and stem 12, and resistance to relative rotation between stem 12 and the humeral bone about longitudinal axis A. As preferred, four grooves 18 are evenly spaced circumferentially about distal portion 16.

The proximal body 20 is generally trapezoidal in cross-section and tapered lengthwise. This configuration conforms to the natural anatomy of the proximal medullary canal of a human humerus and provides increased strength to the proximal body 20. As exemplified in FIG. 4, a typical cross-section of proximal body 29 taken transversely to longitudinal axis A is generally trapezoidal, having rounded corners. Such cross-sectional trapezoids approach a circular configuration at the transition 22 between proximal body 20 and distal portion 16, and increase in anterior-posterior and medial-lateral dimensions in the superior direction by virtue of the aforementioned taper. Proximal body 20 is tapered linearly between the posterior aspect 24 and the anterior aspect 26, in the superior-inferior direction along longitudinal axis A. The designation of the posterior aspect and anterior aspect in the figures is given with reference to an assumed left shoulder implant site. Because the humeral prosthesis 10 is bilaterally symmetrical, it can be implanted at the right shoulder, in which case the designation of the posterior and anterior aspects would be reversed. Between the lateral aspect 28 and the medial aspect 30, proximal body 20 tapers in a curvilinear fashion in the superior-inferior direction along longitudinal axis A by virtue of the arch configuration of the medial aspect 30. The lateral aspect 28 lies substantially parallel to longitudinal axis A. Finally, proximal body 20 is tapered between posterior aspect 24 and anterior aspect 26 in the medial-lateral direction, being wider at the lateral aspect 28 than at the medial aspect 30, resulting in the aforementioned trapezoidal cross-section. Proximal body 20 terminates proximally in a substantially planar surface 32 oriented such that a line normal to surface 32 forms an acute angle relative to longitudinal axis A of about 42 degrees to about 48 degrees, and most preferably about 45 degrees.

Proximal body 20 includes a fin 34 protruding laterally from the otherwise straight lateral aspect 28. Fin 34 is generally triangular in the medial-lateral plane, and has substantially constant width in the anterior-posterior direction. The apex 36 of fin 34 is located nearer to the proximal end than to the distal end of proximal body 20. When the stem 12 is properly implanted within a human humerus, fin 34 resides in the area posterior of the bicipital groove in the greater tuberosity of the human humerus and resists rotation of the implanted stem 12 relative to bone about the longitudinal axis A.

Proximal body 20, as preferred, is dimensioned such that the length of the planar surface 32, in the medial-lateral plane, is between about 0.8 inch and about 1.7 inch, and the width of the planar surface 32 in the anterior-posterior plane is between about 0.30 inch and about 1.2 inch. The axial length of proximal body 20 along the lateral aspect, as preferred, is between about 1.5 inch and about 2.5 inch. The maximum protrusion height of the generally triangular fin 34, as preferred, is between about 0.12 inch and about 0.25 inch.

A plurality of through-holes 38 are provided in fin 34 so that the rotator cuff muscles, the transverse humeral ligament, or other muscles, ligaments, or soft tissues that normally are attached to the head or tuberosities of the humerus can be attached to stem 12 by sutures inserted through one or more of the through-holes 38.

One or more additional through-holes 40, extending from the anterior aspect 26 to the posterior aspect 24 are provided adjacent the arched medial aspect 30 of the proximal body 20. Through hole 40 allows stem 20 to be attached to the proximal end of a resected humerus by an appropriate wire, tape, thread, cord or similar material reeved through through-hole 40 and tied around the proximal end of the natural humerus.

Extending perpendicularly from planar surface 32 of proximal body 20, coaxially with neck axis B, is a male conical taper connector 42. When stem 12 is properly implanted in a human humerus having normal anatomy, neck axis B is located substantially coaxially with the natural axis of the natural humeral head prior to resection.

Head 14 of humeral prosthesis 10 has an articulating surface 44 having a substantially spherical contour. Spherical surface 44 terminates in intersection with the undersurface 46 of head 14. The undersurface 46 comprises a substantially planar surface 48 and a substantially conical surface 50 that intersect in an arc 52. Viewed in a plane perpendicular to planar surface 48 and symmetrically bisecting head 14, conical surface 50 forms an acute angle of about 45 degrees, plus or minus 15°, to the plane of planar surface 48.

Figure 1:
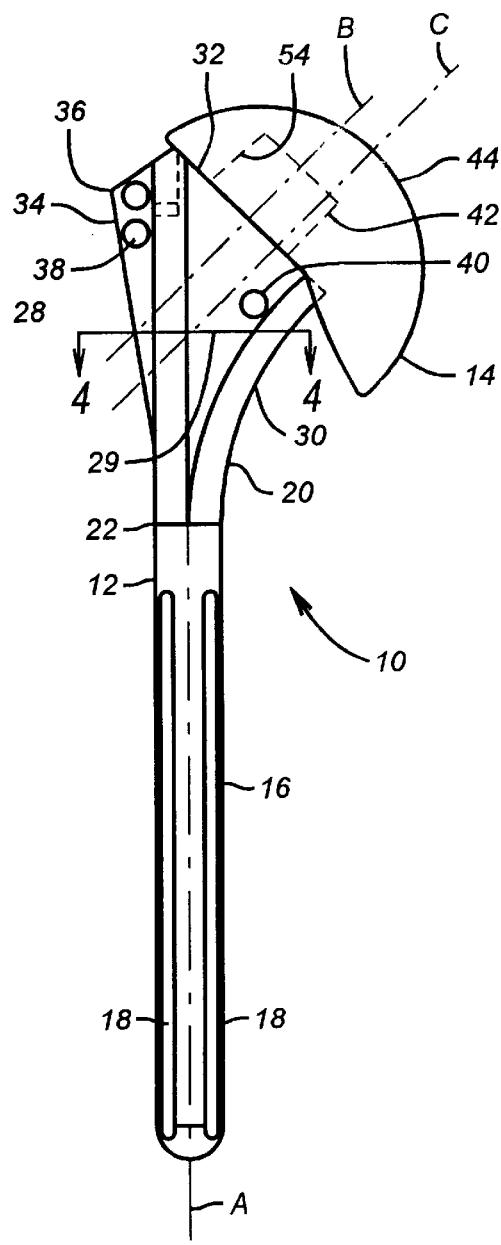
FIG. 1 is a side elevation view of a humeral prosthetic stem and head, constructed according to the present invention.
Figure 3:
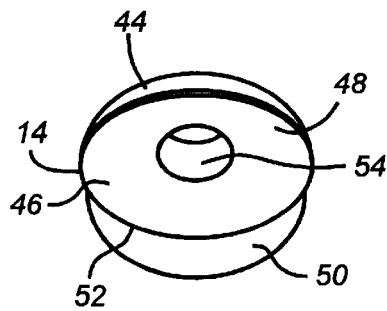
FIG. 3 is a rear elevation view of the head component of the humeral prosthetic stem and head of FIG. 1
Figure 4:
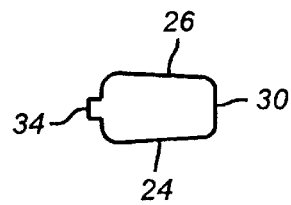
FIG. 4 is a cross-sectional view of the humeral prosthetic stem of FIG. 1, taken in plane 4—4 of FIG. 1 and viewed in the direction of the arrows.

Head 14 further includes a female conical taper recess 54 that opens at planar surface 48, and has a central axis perpendicular to planar surface 48. Female conical taper recess 54 is complementary to the male conical taper 42 such that male taper 42 and female taper 54 comprise a Morse-type taper locking connection when mutually engaged. Once the male taper 42 and the female taper 54 are fully engaged with each other a rigid mechanical coupling is achieved and rotation of head 14 relative to stem 12 is substantially prevented. Nevertheless, by virtue of the Morse-like taperlock connection, the head 14 may be disengaged and removed from stem 12 by application of a sufficient pulling force along axis B. When the male conical taper 42 and the female conical taper 54 are fully engaged with each other as shown in FIG. 1, a small space remains between planar surface 32 and the underside planar surface 48 of head 14. This assures that the head 14 does not bottom out against the stem 12 prior to full engagement of the taperlock connection. When the male and female conical tapers 42 and 54 are engaged, the center of the sphere that the articulating surface 44 of head 14 would form if it were complete, is disposed at or below the planar surface 32 of proximal body 20.

The head 14 is implanted such that the articulating surface 44 is disposed within the glenoid cavity and engages the articulating surface of the glenoid of a human scapula, or alternatively, a prosthetic glenoid surface implanted in the scapula. The surface 44 is highly polished to minimize friction and wear. As preferred, the radius of the spherical articulating surface 44 is in the range from about 0.5 inches to about 1.5 inches.

The spherical articulating surface 44 of head 14 has a radial axis of symmetry C perpendicular to planar undersurface 48 that is offset from the center axis B of the female conical taper recess 54. In other words, the taperlock connector 54 of head 14 is located eccentrically such that the center axis B of the taperlock connector does not pass through the center of curvature of the spherical articulating surface 44. In addition, head 14 includes a skirt comprising conical undersurface 50 extending in a direction away from taperlock connector 54 and articulating surface 44. On that side of head 14 diametrically away from the eccentric location of taperlock connector 54, spherical surface 44 extends inferiorly of the plane of planar undersurface 48. In the orientation shown in FIGS. 1 and 2, head 14 is generally disposed more inferiorly and more medially with respect to stem 12 than it would be if head 14 were not provided with the eccentrically located connector. More particularly, the eccentric location of the taperlock connector 54 results in a more inferior disposition of the proximal edge of head 14 and a more medial disposition of the central portion of articulating surface 44. Likewise, in the orientation shown in FIGS. 1 and 2, the inferior edge of head 14 is disposed more laterally than it would be if head 14 were not provided with the extended articulating surface. Furthermore, the total angle subtended by the spherical articulating surface 44 is increased in the direction of the extension skirt 50, providing a wider range of motion of head 14 in that direction without incurring edge contact between the head 14 and the glenoid or glenoid prosthesis.

Although the direction of the extension skirt 50 is shown lying substantially in the medial-lateral direction in FIGS. 1 and 2, it should be appreciated that the nature of the taperlock connection between head 14 and stem 12 permits head 14 to be rotated about neck axis B prior to full seating of the taperlock connection. Head 14 can be oriented such that the direction of extension skirt 50 is set anteriorly or posteriorly of the medial-lateral direction to accommodate the anatomy of the patient. This is particularly useful for ameliorating the risk of edge contact between the head and glenoid in unusual anatomical situations, or for assuring coverage of posterior cortical bone in patients where the posterior cortical bone of the proximal humerus extends more posteriorly than normal.

While the present invention has been described in terms of a preferred embodiment with particular reference to the drawings, it should be understood that the description is merely exemplary and that the scope of the subject matter that is regarded as the invention is limited only by the appended claims.

I claim:

1. An implantable humeral shoulder prosthesis comprising:

a stem including a distal stem portion having a longitudinal axis and a proximal body, said proximal body including a first connector having a first axis disposed at an acute angle relative to said longitudinal axis; and a head including an undersurface, a spherical articulating surface, including a skirt extending at least about 30 degrees below said undersurface to increase said articulation surface and a radial axis of symmetry that is perpendicular to said undersurface, said head further including at said undersurface a second connector having a second axis;

said first and second connectors being mutually engageable to interlock said head to said proximal body, wherein said first and second axes are concentric with each other and are offset from said radial axis when said first and second connectors are mutually engaged to interlock.

2. The implantable humeral shoulder prosthesis of claim 1, in which said spherical articulating surface of said head has a center of curvature, and said second axis does not pass through said center of curvature.

3. The implantable humeral shoulder prosthesis of claim 1, in which said substantially planar portion and said skirt intersect substantially in an arc.

4. The implantable humeral shoulder prosthesis of claim 1 in which said first and second axes are parallel to said radial axis when said first and second connectors are mutually engaged to interlock.

5. The implantable humeral shoulder prosthesis of claim 4 in which said first axis, said second axis, and said radial axis form an acute angle relative to said longitudinal axis.

6. The implantable humeral shoulder prosthesis of claim 5, in which said spherical articulating surface of said head has a center of curvature, and said axis of said second connector does not pass through said center of curvature.

7. The implantable humeral shoulder prosthesis of claim 6, in which said undersurface of said head includes a substantially planar portion and a substantially conical portion, said substantially conical portion defining a skirt that extends inferiorly of the plane of said substantially planar portion.

8. The implantable humeral shoulder prosthesis of claim 7, in which said substantially planar portion and said substantially conical portion of said undersurface intersect substantially in an arc.

9. The implantable humeral shoulder prosthesis of claim 8, in which said substantially conical portion of said undersurface of said head circumscribes less than about one half of the circumference of the undersurface of said head.

10. The implantable humeral shoulder prosthesis of claim 6 in which said stem transitions from a substantially trapezoidal cross section at said proximal body to a substantially cylindrical cross section at said distal portion.

11. The implantable humeral shoulder prosthesis of claim 10 in which said trapezoidal cross section has rounded corners and tapers in a lengthwise direction.

12. The implantable humeral shoulder prosthesis of claim 6 in which said distal portion has a length between three and six inches and a diameter between 0.25 and 0.75 inches.

13. The implantable humeral shoulder prosthesis of claim 12 in which said distal portion has a plurality of longitudinal, shallow, round-bottomed grooves.

14. The implantable humeral shoulder prosthesis of claim 13 in which said distal portion has four grooves that are evenly and circumferentially spaced.

15. The implantable humeral shoulder prosthesis of claim 5 in which said proximal portion has a lateral side with a fin protruding therefrom, wherein said fin has a triangular configuration in a medial-lateral plane.

16. The implantable humeral shoulder prosthesis of claim 15 in which said fin has a plurality of holes, a constant width, and an apex that is located nearer to said proximal body than to said distal portion.

17. The implantable humeral shoulder prosthesis of claim 5 in which said proximal body of said stem includes at least one hole adjacent an arched medial aspect, said hole extending from an anterior aspect to a posterior aspect.

* * * * *